United States Patent
Suzaki et al.

(10) Patent No.: US 6,652,098 B2
(45) Date of Patent: Nov. 25, 2003

(54) METHOD OF DESIGNING OPHTHALMIC LENS AND OPHTHALMIC LENS PRODUCED BY THE METHOD

(75) Inventors: Asaki Suzaki, Kasugai (JP); Atsushi Kobayashi, Seto (JP)

(73) Assignee: Menicon Co., Ltd., Nagoya (JP)

( * ) Notice: Subject to any disclaimer, the term of this patent is extended or adjusted under 35 U.S.C. 154(b) by 207 days.

(21) Appl. No.: 10/021,507

(22) Filed: Oct. 30, 2001

(65) Prior Publication Data

US 2002/0071092 A1 Jun. 13, 2002

(30) Foreign Application Priority Data

Nov. 1, 2000 (JP) ........................................ 2000-334177
Feb. 26, 2001 (JP) ........................................ 2001-049880

(51) Int. Cl.$^7$ ................................................. G02C 7/02
(52) U.S. Cl. ...................................................... 351/177
(58) Field of Search ................................. 351/177, 159, 351/41, 160 R, 160 H, 161–162; 623/6.11

(56) References Cited

U.S. PATENT DOCUMENTS

| | | | |
|---|---|---|---|
| 5,220,359 A | 6/1993 | Roffman | 351/177 |
| 5,235,357 A * | 8/1993 | Winthrop et al. | 351/159 |
| 6,082,856 A | 7/2000 | Dunn et al. | 351/160 H |
| 6,089,711 A | 7/2000 | Blankenbecler et al. | 351/160 R |
| 6,224,211 B1 * | 5/2001 | Gordon | 351/177 |

FOREIGN PATENT DOCUMENTS

| | | |
|---|---|---|
| JP | B2-2859092 | 12/1998 |
| JP | B2-2913191 | 4/1999 |
| JP | B2-3022640 | 1/2000 |

* cited by examiner

*Primary Examiner*—Jordan M. Schwartz
(74) *Attorney, Agent, or Firm*—Burr & Brown

(57) ABSTRACT

A method of designing an ophthalmic lens, including: determining specifications of a temporary lens to provide an optical power required by a wearer; applying the temporary lens to a prescribed schematic eye, and effecting emmetropization of an optical system including the temporary lens and schematic eye; obtaining an optical characteristic of the optical system at a position of an optical axis of the temporary lens which is offset from an optical axis of the schematic eye by an offset amount; obtaining successively optical characteristics corresponding to different configurations of the temporary lens with the axes of the temporary lens and schematic eye offset by the offset amount; selecting optimum one of the different configurations of the temporary lens which gives optimum one of the successively obtained optical characteristics; and determining specifications of an intended ophthalmic lens as a final product, based on the selected optimum configuration of the temporary lens.

22 Claims, 5 Drawing Sheets

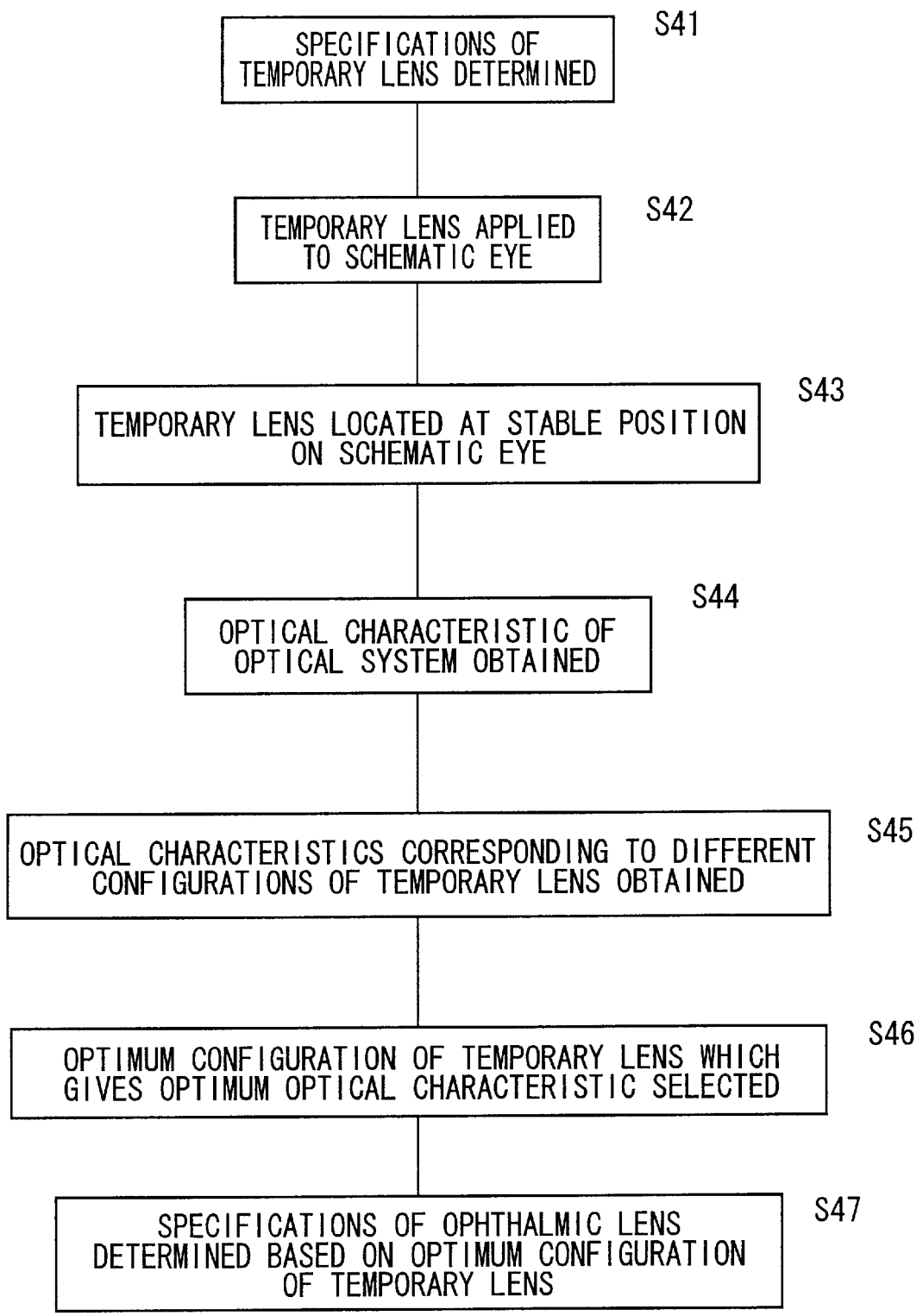

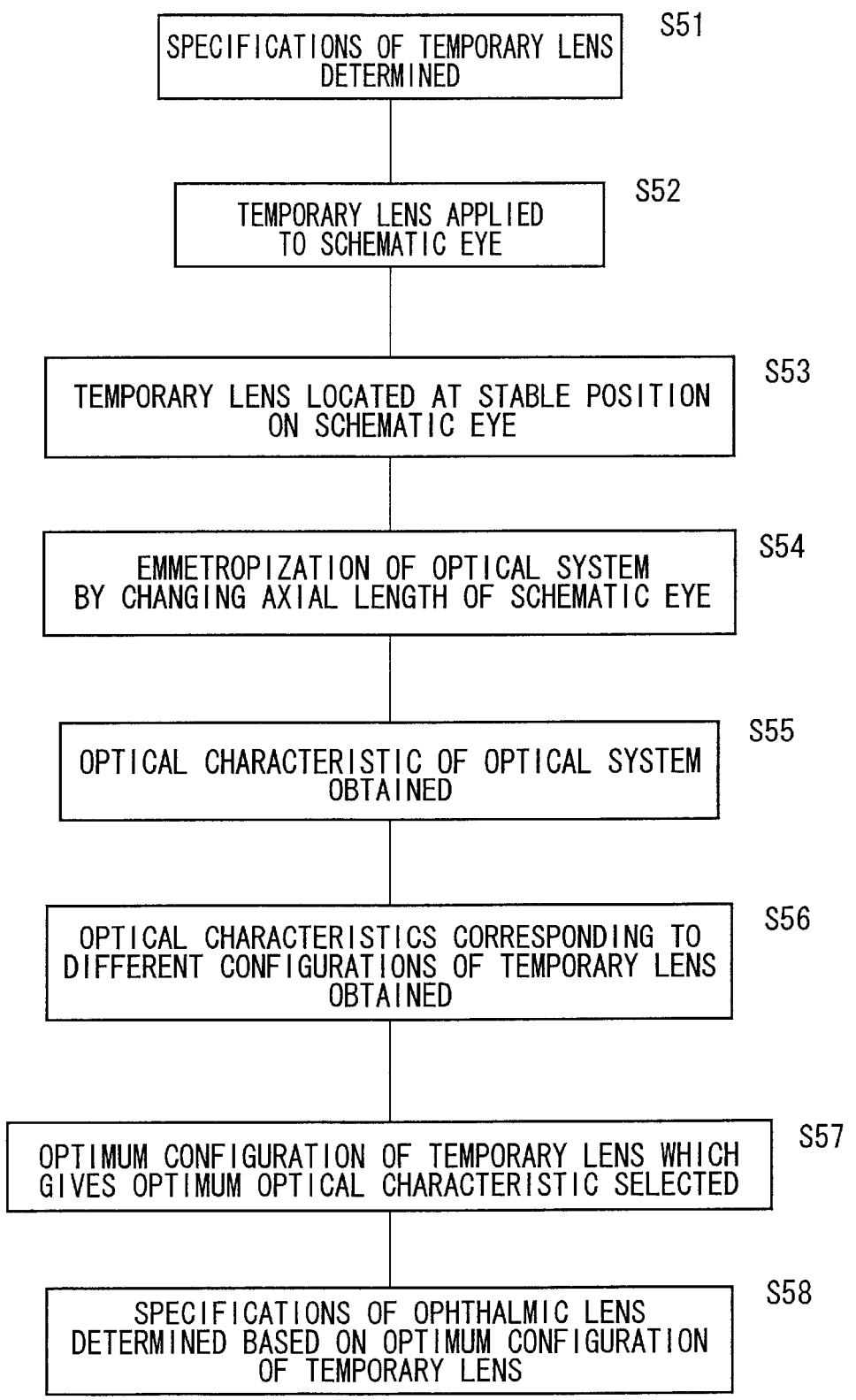

METHOD OF DESIGNING OPHTHALMIC LENS AND OPHTHALMIC LENS PRODUCED BY THE METHOD

This application is based on Japanese Patent Application Nos. 2000-334177 filed Nov. 1, 2000, and 2001-049880 filed Feb. 26, 2001, the contents of which are incorporated hereinto by reference.

BACKGROUND OF THE INVENTION

1. Field of the Invention

The present invention relates in general to a novel method of designing an ophthalmic lens, and an ophthalmic lens produced by the method. More particularly, the present invention is concerned with a method of determining specifications of the ophthalmic lens, which ophthalmic lens assures a high degree of visual acuity with high stability while avoiding a variation of the visual acuity even when the optical axis of the ophthalmic lens is offset from the optical axis of the eye of the lens wearer due to a movement of the lens on the cornea or in the eye. Further, the present invention is concerned with a method of producing the ophthalmic lens based on the determined specifications. The present invention also relates to an ophthalmic lens which is produced by the method.

2. Discussion of Related Art

Conventionally, an ophthalmic lens such as a contact lens and an intraocular lens is designed independently of the eye to which the ophthalmic lens is applied. In other words, the ophthalmic lens is produced so as to assure an optimum characteristic of imaging on its optical axis. For attaining the optimum imaging characteristic, various techniques are proposed. For instance, Japanese Patent No. 2859092 discloses a method of designing an ophthalmic lens, wherein a path of light which is incident on each reference point on one of the opposite lens surfaces that has been already formed into an intended configuration is taken into account, and an angle of inclination of the other lens surface at a point located on the light path is determined so that the light undergoes an intended refracting force. Japanese Patent No. 2913191 discloses a method of designing a lens by a ray tracing technique in an attempt to reduce a spherical aberration of the lens. In the disclosed method, the configuration of the refracting surface of the lens is designed as follows. The inclination of a curved surface at an arbitrary height as measured from the optical axis of the refracting surface is determined such that the light passing the arbitrary height passes a desired final pass point which is set in advance, after the light has passed through the lens. Based on the successively obtained inclinations of the curved surface at different heights, the configuration of the curved surface as a whole is designed.

Japanese Patent No. 3022640 discloses a method of producing an aspheric lens, comprising the steps of: constructing a mathematical model of a system of a human eye and a preliminary lens; performing an analysis using the model to trace light ray paths through the lens-eye system; varying a value of the aspheric constant k for the preliminary lens to achieve a lens-eye system with a trace of light ray paths optimized for sharpest focus by minimizing retinal spot size of the rays.

The above-described conventional methods of designing or producing the ophthalmic lens aim at optimizing the imaging characteristic on the optical axis of the lens. These methods are for optimizing the imaging characteristic with respect to an optical schematic of the human eye (schematic eye) by taking into account the eye optical system. The ophthalmic lens designed or produced according to the conventional methods assures the optimum imaging characteristic on its optical axis. These methods, however, ignore the fact that the center of the pupil of the eye (the optical axis of the eye) is usually not aligned with the optical center of the lens while the lens is applied to or worn on the eye. Accordingly, the optical characteristic of the optical system consisting of the lens and the eye tends to be deteriorated when the lens is offset from the optical axis of the eye. For example, the optical center of the contact lens is not aligned with the center of the pupil of the eye in most instances when the contact lens is worn on the eye. The movement of the contact lens on the cornea of the lens wearer's eye and the stable position of the contact lens on the cornea in which the contact lens is stably held in place vary depending upon the individual lens wearers. Accordingly, the visual acuity and stability tend to fluctuate depending upon the movement and stable position of the contact lens on the cornea of the eye.

SUMMARY OF THE INVENTION

The present invention was developed in the light of the background art described above. It is therefore a first object of the invention to provide a method of designing an ophthalmic lens which exhibits optical characteristics equal to or close to those exhibited by the ophthalmic lens when its optical axis is aligned with the optical axis of the eye on which the ophthalmic lens is worn, or in which the ophthalmic lens is inserted, even if the optical axis of the ophthalmic lens is displaced or offset from that of the eye.

It is a second object of the invention to provide a method of producing an intended ophthalmic lens by the designing method described above.

It is a third object of the invention to provide an ophthalmic lens produced by the designing method described above.

The first object indicated above may be achieved according to a first aspect of the present invention, which provides a method of designing an ophthalmic lens, comprising the steps of: determining specifications of a temporary lens such that said temporary lens gives an optical power required by a wearer of the ophthalmic lens; applying said temporary lens to a prescribed schematic eye, and effecting emmetropization of an optical system consisting of said temporary lens and said schematic eye; obtaining an optical characteristic of said optical system at a position of an optical axis of said temporary lens which is offset from an optical axis of said schematic eye by a predetermined offset amount; obtaining successively optical characteristics corresponding to different configurations of said temporary lens with said axes of said temporary lens and said schematic eye being offset from each other by said predetermined offset amount; selecting optimum one of said different configurations of said temporary lens which gives optimum one of the successively obtained optical characteristics; and determining specifications of an intended ophthalmic lens as a final product, based on the selected optimum configuration of said temporary lens.

In the present method described above, the optical characteristic of the optical system consisting of the schematic eye and the temporary lens is obtained with the temporary lens being applied to the schematic eye. Further, the optical characteristic of the optical system is obtained at the position of the optical axis of the temporary lens which is offset from the optical axis of the schematic eye by the predetermined offset amount that is expected when the ophthalmic lens is actually applied to the eye of the lens wearer. The optical characteristics of the optical system are successively obtained corresponding to different configurations of the temporary lens, and the optimum one of the different configurations of the temporary lens which gives the optimum one of the successively obtained optical characteristics is selected. On the basis of the selected configuration of the temporary lens, the specifications of the intended ophthalmic lens are determined. Accordingly, the ophthalmic lens whose specifications are determined based on the optimum configuration of the temporary lens which gives the optimum optical characteristic assures an excellent optical characteristic even if the optical axis of the ophthalmic lens is offset from that of the lens wearer's eye while the ophthalmic lens is actually applied to the eye. Therefore, the visual acuity and stability can be effectively enhanced.

The above-indicated first object of the present invention may also be achieved according to a second aspect of the invention, which provides a method of designing an ophthalmic lens, comprising the steps of: determining specifications of a temporary lens such that the temporary lens gives an optical power required by a wearer of the ophthalmic lens; applying the temporary lens to a prescribed schematic eye, and effecting emmetropization of an optical system consisting of the temporary lens and the schematic eye; obtaining, as a reference characteristic, an optical characteristic of the optical system at a position of an optical axis of the temporary lens which is aligned with an optical axis of the schematic eye; obtaining, as a variable characteristic, an optical characteristic of the optical system at a position of the optical axis of the temporary lens which is offset by a predetermined offset amount from the optical axis of the schematic eye; obtaining successively the reference characteristics and the variable characteristics corresponding to different configurations of the temporary lens; selecting one of the different configurations of the temporary lens, which gives a minimum difference between the reference characteristic and the variable characteristic; and determining specifications of an intended ophthalmic lens as a final product, based on the selected configuration of the temporary lens.

In the present method described above, the optical characteristic of the optical system consisting of the schematic eye and the temporary lens which is applied thereto is obtained as the reference characteristic when the emmetropization of the optical system is established. Further, the optical characteristic of the optical system is obtained as the variable characteristic when the optical axis of the temporary lens is offset by the predetermined offset amount from the optical axis of the schematic eye. The reference characteristics and variable characteristics are successively obtained corresponding to different configurations of the temporary lens. From among the different configurations of the temporary lens, one of the configurations of the temporary lens which gives a minimum difference between the reference and variable characteristics is selected. On the basis of the selected configuration of the temporary lens which gives the minimum difference between the reference and variable characteristics, the specifications of the intended ophthalmic lens are determined. Therefore, the ophthalmic lens designed according to the present method described above assures an improved optical characteristic even when the optical axis of the lens is offset from that of the eye to which the ophthalmic lens is applied.

The above-indicated first object of the invention may also be attained according to a third aspect of the invention, which provides a method of designing an ophthalmic lens, comprising the steps of: determining specifications of a temporary lens such that the temporary lens gives an optical power required by a wearer of the ophthalmic lens; applying the temporary lens to a prescribed schematic eye such that the temporary lens is located at a position on the schematic eye corresponding to a stable position on an eye of the wearer in which the ophthalmic lens is held in place; obtaining an optical characteristic of an optical system consisting of the temporary lens and the schematic eye with the temporary lens being located at the stable position on the schematic eye, obtaining successively optical characteristics corresponding to different configurations of the temporary lens; selecting optimum one of the different configurations of the temporary lens which gives optimum one of the successively obtained optical characteristics; and determining specifications of an intended ophthalmic lens as a final product, based on the selected optimum configuration of the temporary lens.

In the present method described above, the optical characteristic of the optical system consisting of the temporary lens and the schematic eye is obtained with the temporary lens being located at the stable position on the schematic eye corresponding to the stable position on the lens wearer's eye in which the ophthalmic lens is held in place. In other words, the optical characteristic of the optical system is obtained at a position of the optical axis of the temporary lens which is offset from the optical axis of the schematic eye by the predetermined offset amount that is expected when the ophthalmic lens is actually applied to the lens wearer's eye. The optical characteristics of the optical system are successively obtained corresponding to different configurations of the temporary lens. In the present method, the optimum one of the different configurations of the temporary lens which gives the optimum one of the successively obtained optical characteristic is selected, and the specifications of the intended ophthalmic lens are determined on the basis of the selected optimum configuration of the temporary lens which gives the optimum optical characteristic. Accordingly, the ophthalmic lens whose specifications are determined based on the optimum configuration of the temporary lens which gives the optimum optical characteristic assures an excellent optical characteristic even if the optical axis of the ophthalmic lens is offset from that of the wearer's eye while the ophthalmic lens is actually applied to the eye. Therefore, the visual acuity and stability can be effectively enhanced.

The above-indicated first object of the invention may also be attained according to a fourth aspect of the invention, which provides a method of designing an ophthalmic lens, comprising the steps of: determining specifications of a temporary lens such that the temporary lens gives an optical power required by a wearer of the ophthalmic lens; applying the temporary lens to a prescribed schematic eye such that the temporary lens is located at a position on the schematic eye corresponding to a stable position on an eye of the wearer in which the ophthalmic lens is held in place, and effecting emmetropization of the optical system with the temporary lens being located at the stable position on the schematic eye; obtaining an optical characteristic of the optical system while the emmetropization of the optical system is established, obtaining successively optical characteristics corresponding to different configurations of the temporary lens; selecting optimum one of the different configurations of the temporary lens which gives optimum one of the successively obtained optical characteristics; and determining specifications of an intended ophthalmic lens as a final product, based on the selected optimum configuration of the temporary lens.

In the present method described above, the temporary lens is located at the stable position on the schematic eye corresponding to the stable position on the lens wearer's eye in which the ophthalmic lens is held in place. The optical characteristic of the optical system consisting of the schematic eye and the temporary lens which is located at the stable position on the schematic eye is obtained while the emmetropization of the optical system is established. The optical characteristics are successively obtained corresponding to the different configurations of the temporary lens while the emmetropization of the optical system is established. In the present method, the optimum one of the different configurations of the temporary lens which gives the optimum one of the successively obtained optical characteristics is selected, and the specifications of the intended ophthalmic lens are determined on the basis of the selected optimum configuration of the temporary lens which gives the optimum optical characteristic. Accordingly, the present method permits an easy and advantageous designing of the ophthalmic lens which exhibits an excellent optical characteristic.

In one preferred form of the above-described first and second aspects of the invention, the emmetropization of the optical system is effected with the optical axes of the temporary lens and the schematic eye being aligned with each other.

In one preferred form of the above-described first, second and fourth aspects of the invention, the emmetropization of the optical system is effected by changing at least one of the following parameters selected from the group consisting of: an axial length of the schematic eye, a radius of curvature of a front surface of a cornea of the schematic eye, a radius curvature of a back surface of the cornea of the schematic eye, a radius of curvature of a front surface of a crystalline lens of the schematic eye, a radius of curvature of a back surface of the crystalline lens of the schematic eye, a diameter of a pupil of the schematic eye, and an optical power of a corrective lens.

In the above-described methods according to the first through fourth aspects of the invention, the optical characteristics of the optical system is preferably calculated by at least one of a wavefront aberration, a point spread function (PSF), a modulation transfer function (MTF), and a resolving power, for thereby facilitating a mathematical analysis of the optical characteristic of the optical system.

In another preferred form of the above-indicated first through fourth aspects of the invention, the schematic eye corresponds to an eye of the wearer who wears the ophthalmic lens.

In yet another preferred form the above-indicated first and second aspects of the invention, the ophthalmic lens is a contact lens, and the predetermined offset amount of the optical axis of the temporary lens from the optical axis of the schematic eye is not greater than 30°. The predetermined offset amount is preferably divided into a plurality of divisions, each division being not greater than 10°, and the optical characteristic is obtained at an end point of each of the plurality of divisions. According to this arrangement, the optimum optical characteristic is advantageously selected by taking into account the optical characteristics obtained at the respective end points of the plurality of divisions of the offset amount.

In a further preferred form the above-indicated first and second aspects of the invention, the ophthalmic lens is an intraocular lens, and the predetermined offset amount of the optical axis of the temporary lens from the optical axis of the schematic eye is not greater than 4 mm. The predetermined offset amount is preferably divided into a plurality of divisions, each division being not greater than 2 mm, and the optical characteristic is obtained at an end point of each of the plurality of divisions. According to this arrangement, the optimum optical characteristic is advantageously selected by taking into account the optical characteristics obtained at the respective end points of the plurality of divisions.

The above-described second object of the invention may be attained according to a fifth aspect of the invention, which provides a method of producing an ophthalmic lens based on the specifications determined by any one of the methods according to the first through fourth aspects of the invention described above. The ophthalmic lens produced by the present method exhibits an excellent optical characteristic.

The above-indicated third object of the invention may be attained according to a sixth aspect of the invention, which provides an ophthalmic lens produced by any one of the methods according to the first through fourth aspects of the invention described above. The present ophthalmic lens assures improved visual acuity and stability even if the optical axis of the ophthalmic lens is offset from the optical axis of the eye of the lens wearer.

BRIEF DESCRIPTION OF THE DRAWINGS

The above and other objects, features, advantages and technical and industrial significance of the present invention will be better understood by reading the following detailed description of presently preferred embodiments of the invention, when considered in connection with the accompanying drawings, in which:

FIG. 4 is a flow chart illustrating steps for designing an ophthalmic lens according to a fourth embodiment of the invention; and FIG. 5 is a flow chart illustrating steps for designing an ophthalmic lens according to a fifth embodiment of the invention.

DETAILED DESCRIPTION OF PREFERRED EMBODIMENTS

Figure 1:
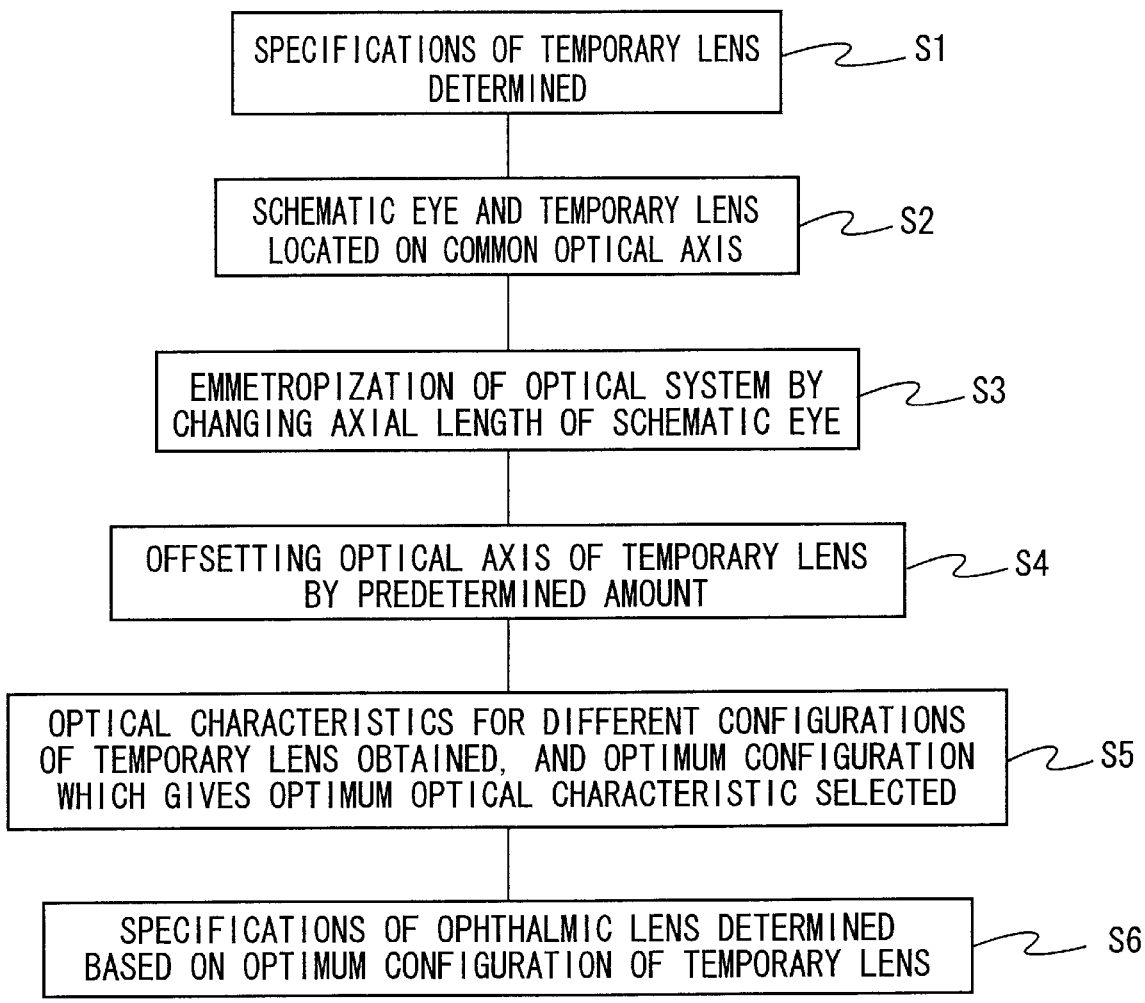
FIG. 1 is a flow chart illustrating steps for designing an ophthalmic lens according to a first embodiment of the invention.

Referring first to a flow chart of FIG. 1, there are shown steps for designing an ophthalmic lens according to a first embodiment of the present invention. The flow chart starts with step S1 in which the specifications of a temporary or trial lens which gives the intended ophthalmic lens are determined such that the temporary lens gives an optical power required by a wearer of the ophthalmic lens. The optical power required by the lens wearer is determined by various examinations of the eye to which the intended ophthalmic lens is applied, using various known devices. Based on the knowledge of those skilled in the art of the ophthalmic lens, the configuration of the temporary lens is temporaryly determined, and the specifications of the temporary lens such as a base curve (BC) of a back surface, a front curve (FC) of a front surface, a diameter (DIA), a center thickness (CT), an aspheric coefficient, etc. are determined by taking into account a refractive index of a lens material.

Step S1 is followed by step S2 in which the temporary lens and a suitable schematic eye are located on a common optical axis. In other words, the temporary lens is applied to the schematic eye with their optical axes being aligned with each other. The temporary lens applied to the schematic eye is mathematically expressed for calculating the optical characteristic described below.

As the schematic eye used in the present embodiment, various known schematic eyes can be employed. In the present embodiment, the Gullstrand Schematic Eye at non-accommodating state having the following parameters is used.

(1) Radius of curvature (mm)
  cornea front surface/back surface: 7.7/6.8
  crystalline lens front surface/back surface: 10.0/−6.0
(2) Position of the refracting surface (mm)
  cornea front surface/back surface: 0.0/0.5
  crystalline lens front surface: 3.6
  crystalline lens back surface: 7.2
  macula: 24.0
(3) Refractive index
  cornea: 1.376
  aqueous humor: 1.336
  crystalline lens: 1.386

In the present embodiment, the values of any one of the parameters (1)–(3) may be replaced with those obtained from the eye of the lens wearer, so that the known schematic eye is approximated to the eye of the lens wearer. The schematic eye which approximates the lens wearer's eye can be used in the present embodiment in place of the known schematic eye such as the Gullstrand Schematic Eye described above. The schematic eye which approximates the lens wearer's eye is obtained, for instance, on the basis of the radii of curvature of the front and back surfaces of the cornea and the radii of curvature of the front and back surfaces of the crystalline lens measured from the lens wearer's eye. Alternatively, the schematic eye which approximates the lens wearer's eye is obtained on the basis of the positions of refracting surface measured from the lens wearer's eye by utilizing the ultrasonic wave. The thus obtained schematic eye approximating the lens wearer's eye permits a higher degree of accuracy in designing the ophthalmic lens.

Step S2 is followed by step S3 in which the emmetropizaion of the optical system consisting of the schematic eye and the temporary lens whose optical axes are aligned with each other is effected by changing an axial length of the schematic eye, for thereby permitting an image to be formed on the retina of the schematic eye (i.e., locating an image surface on the retina).

Step S3 is followed by step S4 in which the position of the optical axis of the temporary lens is offset by a predetermined offset amount from the optical axis of the schematic eye, and the optical characteristic of the optical system consisting of the schematic eye and the temporary lens is obtained at the position of the optical axis of the temporary lens which is offset from the optical axis of the schematic eye by the predetermined offset amount. In general, this offset amount is determined based on an average value of the offset amounts corresponding to the different stable positions of the ophthalmic lens on the ordinary lens wearers' eyes, or a maximum value of the offset amount. When the ophthalmic lens is a contact lens, the offset amount represented by an angle defined by the intersecting optical axes of the contact lens and the schematic eye is determined to be not greater than 30°. When the ophthalmic lens is an intraocular lens, the offset amount represented by a distance between the optical axes of the intraocular lens and the schematic eye as measured on the cornea of the schematic eye is determined to be not greater than 4 mm.

Step S4 is followed by step S5 in which the optical characteristics of the optical system consisting of the schematic eye and the temporary lens whose optical axes are offset from each other by the predetermined offset amount are successively obtained corresponding to different configurations of the temporary lens. From among the different configurations of the temporary lens, the optimum configuration which gives optimum one of the successively obtained optical characteristics is selected.

In step S5, the optical characteristics of the optical system are obtained corresponding to the different configurations of the temporary lens in which at least one parameter of the specifications is changed. In view of the fact that the base curve (BC) of the back surface of the contact lens is generally determined so as to match the radius of curvature of the lens wearer's eye, it is preferable to keep the base curve at a constant value. Accordingly, other parameters such as the front curve (FC) of the front surface, the center thickness (CT), and the aspheric coefficient of the temporary lens are changed to give the different configurations of the temporary lens.

The optical characteristic of the optical system consisting of the temporary lens and the schematic eye obtained in step S5 is represented by a numerical value calculated by a wavefront aberration, a PSF (Point Spread Function), or a MTF (Modulation Transfer Function), which are relevant to one another, or a numerical value of a resolving power. The wavefront aberration, PSF, MTF, and resolving power are functions known in the art indicative of the optical characteristic. The wavefront aberration is recognized as a deviation of a wavefront which has passed through an optical system, from an ideal wavefront, and obtained as a difference between the wavefront obtained by a ray tracing technique and a reference wavefront whose center lies at an ideal image point. The PSF is recognized as a function representing an intensity distribution of an image of a point object in an object space, which is formed on an image surface formed by the optical system. The PSF is represented by the point image intensity distribution I (x, y) calculated by the following formula:

$$a(x, y) = \frac{1}{S} \int\!\!\int_{-\infty}^{\infty} \exp\left[i\left\{\frac{2\pi}{\lambda} W(\xi, \eta) - (x\xi + y\eta)\right\}\right] d\xi d\eta$$

$$I(x, y) = a(x, y) \cdot a^*(x, y)$$

wherein:
  $a^*(x, y)$ is a conjugate complex number of $a(x, y)$,
  $(x, y)$ are coordinate values of a point in the vicinity of the image point,
  W is a pupil function,
  $(\xi, \eta)$ are coordinate values of the pupil
  S is a surface area of the pupil
  $\pi$ is a ratio of the circumference of a circle to its diameter,
  $\lambda$ is a wavelength, and
  i is an imaginary number.

The MTF is recognized as a function of a spatial frequency which represents a change of a contrast of an image in a sinusoidal wave pattern. The MTF is generated by Fourier transformation of the point image intensity distribution I (x, y) of the PSF.

The resolving power is recognized as a quantity indicative of a performance of a lens, and is indicated by an inverse number of a minimum width (mm) of a pair of black and white images distinguished in a test target.

The calculation of the optical characteristic is known in the art, and is effected by using commercially available software packages such as "OSLO SIX" available from Sinclair Optics, Inc., and "ZEMAX" available from Focus Software, Inc.

The optical characteristics are successively obtained corresponding to different configurations of the temporary lens whose optical axis is offset from the optical axis of the schematic eye by the predetermined offset amount. From among the successively obtained optical characteristics, the optimum one of the optical characteristics is selected, and one of the different configurations of the temporary lens which gives the optimum optical characteristic is determined.

Step S5 is followed by Step S6 to determine the specifications (such as BC, FC, DIA, CT, and aspheric coefficient) of an intended ophthalmic lens based on the selected optimum configuration of the temporary lens.

In the method of designing the ophthalmic lens wherein the specifications of the intended ophthalmic lens are determined according to the flow chart of FIG. 1 of the first embodiment of the invention, the offset amount of the optical axis of the ophthalmic lens from the center of the pupil (the optical axis of the schematic eye) is determined by taking into account the stable position of the ophthalmic lens on the eye model (the schematic eye), in which the lens is stably held in place. The optical characteristics corresponding to the different configurations are obtained with the optical axis of the temporary lens being offset from the optical axis of the schematic eye by the offset amount determined as described above. In the present method, the optimum one of the different configurations of the temporary lens which gives the optimum one of the plurality of optical characteristics is selected, and the specifications of the intended ophthalmic lens are determined on the basis of the selected optimum configuration of the temporary lens. Accordingly, the ophthalmic lens whose specifications are determined as described above exhibits an excellent optical characteristic irrespective of the movement of the ophthalmic lens on the lens wearer's eye to which the lens is applied. Therefore, the ophthalmic lens designed as described above effectively assures improved visual acuity and stability.

Figure 2:
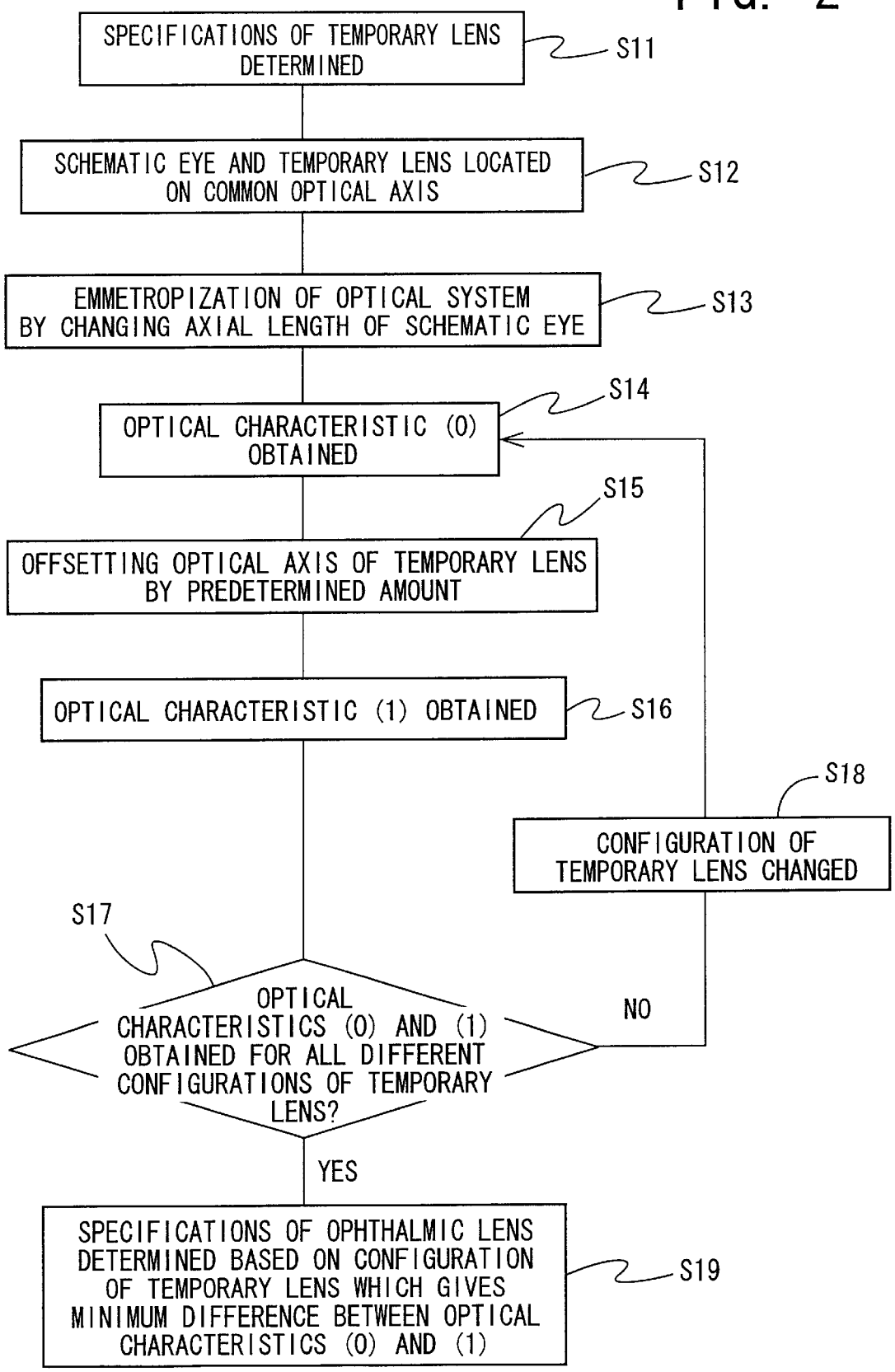
FIG. 2 is a flow chart illustrating steps for designing an ophthalmic lens according to a second embodiment of the invention.

Referring next to the flow chart of FIG. 2, there is shown another method of designing an ophthalmic lens according to a second embodiment of the invention.

The flow chart of FIG. 2 is identical with the flow chart of FIG. 1, except for steps S14 through S18. Steps S11 through S13 and step S19 in the flow chart of FIG. 2 correspond to Steps S1 through S3 and step S6 in the flow chart of FIG. 1, respectively.

In steps S11 through S13 in the flow chart of FIG. 2 corresponding to steps S1 through S3 in the flow chart of FIG. 1, the temporary lens is applied to the prescribed schematic eye such that the optical axis of the temporary lens is aligned with that of the schematic eye, and the optical system consisting of the temporary lens and the schematic eye is subjected to the emmetropization. In the following step S14, the optical characteristic (0) of the optical system is obtained as a reference characteristic.

Step S14 is followed by step S15 in which the position of the optical axis of the temporary lens is offset from the optical axis of the schematic eye by a predetermined offset amount that is expected when the ophthalmic lens such as a contact lens or an intraocular lens is actually applied to the eye of the lens wearer. In the following step S16, the optical characteristic (1) of the optical system is obtained as a variable characteristic, at the position of the optical axis of the temporary lens which is offset by the predetermined offset amount from the optical axis of the schematic eye.

Steps S14 through S16 are repeatedly executed to obtain a plurality of pairs of the reference characteristic (0) and the variable characteristic (1) corresponding to different configurations of the temporary lens. To this end, step S16 is followed by step S17 to determine whether the reference and variable characteristics have been obtained for all of the different configurations of the temporary lens. If a negative decision (NO) is obtained in step S17, the control flow goes to step S18 to change the configuration of the temporary lens, namely, to select the next configuration of the temporary lens. If it is determined in step S17 that the reference and variable characteristics have been obtained for all of the different configurations of the temporary lens, step S19 is implemented to first select one of the different configurations of the temporary lens which gives one of the plurality of pairs of the reference and variable characteristics whose difference is minimum, and then determine the specifications of the intended ophthalmic lens, based on the selected configuration of the temporary lens which gives the minimum difference between the reference and variable characteristics.

In the method of designing the ophthalmic lens according to the flow chart of FIG. 2 of the second embodiment of the invention, the reference characteristic (0) of the optical system is obtained while the emmetropization of the optical system is established, and the variable characteristic (1) of the optical system is obtained at the position of the optical axis of the temporary lens which is offset by the predetermined offset amount from the optical axis of the schematic eye. These reference characteristic (0) and variable characteristic (1) are obtained for every one of the different configurations of the temporary lens. Among the configurations of the temporary lens, one of the configurations which gives a minimum difference between the reference and variable characteristics is selected. On the basis of the selected configuration of the temporary lens, the specifications of the intended ophthalmic lens are determined. According to this arrangement, the ophthalmic lens having an improved lens characteristic can be designed with high accuracy. Therefore, the ophthalmic lens designed according to the present method exhibits a lens characteristic equal to, or close to that of the ophthalmic lens when its optical axis is aligned with the optical axis of the eye, even if the optical axis of the ophthalmic lens is offset or moved from the optical axis of the eye to which the ophthalmic lens is applied.

If the offset amount of the optical axis of the temporary lens from the optical axis of the schematic eye is relatively large, the offset amount may be divided into a plurality of divisions, and the optical characteristic of the optical system consisting of the temporary lens and schematic eye is obtained at an end point of each of the plurality of divisions. In this case, an effective lens characteristic can be obtained by taking into account a plurality of optical characteristics obtained at the respective end points of the plurality of divisions of the offset amount. One example of this arrangement is shown in a flow chart of FIG. 3 according to a third embodiment of the invention.

Figure 3:
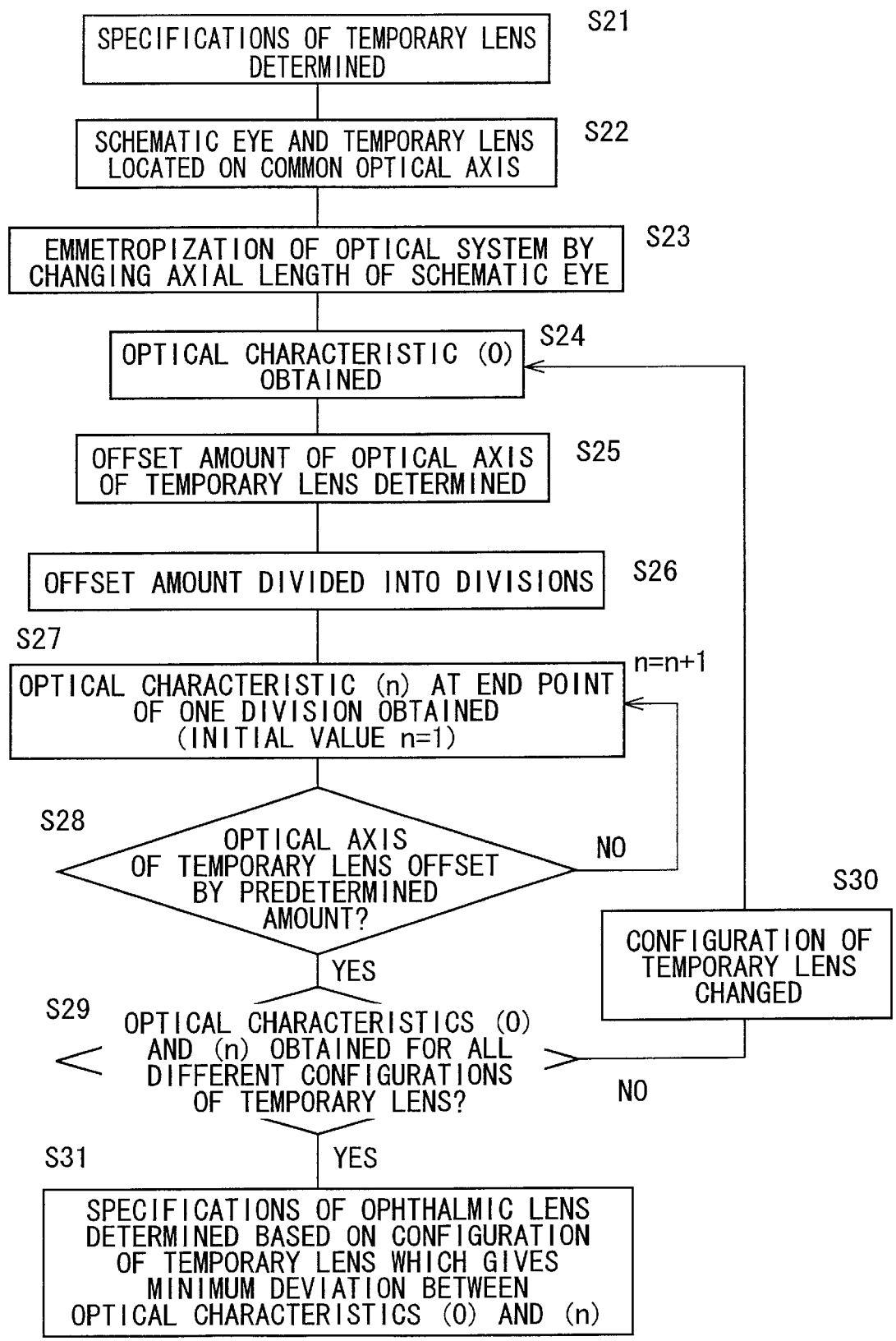
FIG. 3 is a flow chart illustrating steps for designing an ophthalmic lens according to a third embodiment of the invention.

In steps S21 through S23 of the flow chart of FIG. 3 corresponding to steps S1 through S3 of the flow chart of FIG. 1, the emmetropization of the optical system consisting of the schematic eye and the temporary lens is effected with the optical axes of the schematic eye and the temporary lens being aligned with each other. In the following step S24, the optical characteristic (0) of the optical system is obtained while the emmetropization of the optical system is established.

Step S24 is followed by step S25 in which the offset amount of the optical axis of the temporary lens from the optical axis of the schematic eye is determined. The offset amount is suitably determined depending upon the kind of the ophthalmic lens. When the ophthalmic lens is a contact lens, the offset amount represented by an angle defined by the intersecting optical axes of the contact lens and the schematic eye is determined to be not greater than 30°. When the ophthalmic lens is an intraocular lens, the offset amount represented by a distance between the optical axes of the intraocular lens and the schematic eye as measured on the cornea of the schematic eye is determined to be not greater than 4 mm.

Step S25 is followed by step S26 in which the determined offset amount is divided into a plurality of divisions. The amount of each division is suitably determined depending upon the kind of the ophthalmic lens. When the ophthalmic lens is a contact lens, the amount of each division represented by an angle defined by the intersecting optical axes of the schematic eye and the temporary lens is not greater than 10°, and the optical characteristic of the optical system is obtained at an end point of each of the plurality of divisions. When the ophthalmic lens is an intraocular lens, the amount of each division represented by a distance between the optical axes of the schematic eye and the temporary lens is not greater than 2 mm as measured on the cornea of the schematic eye, and the optical characteristic of the optical system is obtained at en end point of each of the plurality of divisions.

Step S26 is followed by step S27 in which the optical characteristic (n) of the optical system is obtained, at a position of the optical axis of the temporary lens which is offset from the optical axis of the schematic eye by a distance corresponding to one of the plurality of divisions_ of the offset amount determined in step S26.

Step S27 is followed by step S28 to determine whether the optical axis of the temporary lens has been offset from the optical axis of the schematic lens by the offset amount determined in step S25. If a negative decision (NO) is obtained in step S28, the control flow goes back to step S27 to offset the optical axis of the temporary lens by a further distance corresponding to one division of the offset amount, and the optical characteristic (n) of the optical system is obtained at the position of the optical axis of the temporary lens which is offset from the optical axis of the schematic lens by a total distance corresponding to two divisions of the offset amount. In essence, steps S27 and S28 are repeatedly executed until the position of the optical axis of the temporary lens is offset from the optical axis of the schematic lens by the predetermined offset amount determined in step S25, and the optical characteristic (n) of the optical system is obtained at the end point of each of a plurality of divisions.

If an affirmative decision (YES) is obtained in step S28, namely, when the position of the optical axis of the temporary lens has been offset from the optical axis of the schematic eye by the predetermined offset amount, step S29 is executed to determine whether the optical characteristics (0) and (n) have been obtained for all of different configurations of the temporary lens. If a negative decision (NO) is obtained in step S29, the control flow goes to step S30 to change the configuration of the temporary lens, namely, to select the next configuration of the temporary lens. Steps S24 through S30 are repeatedly executed so as to obtain a plurality of pairs of the optical characteristics (0) and (n) corresponding to all of the different configurations of the temporary lens.

If an affirmative decision (YES) is obtained in step S29, the control flow goes to step S31 to select one of the different configurations of the temporary lens which gives one of the plurality of pairs of the optical characteristics (0) and (n) whose deviation is minimum. On the basis of the selected configuration of the temporary lens, the specifications of an intended ophthalmic lens are determined also in step S31.

In the method of designing the ophthalmic lens according to the flow chart of FIG. 3 of the third embodiment of the invention, the optical characteristics (0) as the reference characteristic and the optical characteristics (n) as the variable characteristic are obtained corresponding to the different configurations of the temporary lens, and one of the different configurations of the temporary lens is selected, which configuration gives one of the plurality of pairs of the optical characteristics (0) and (n) whose deviation is minimum. In the present embodiment wherein the optical characteristics (n) are obtained at the respective end points of the plurality of divisions of the offset amount, it is easy to select the above-indicated one pair of the optical characteristics (0) and (n) whose deviation is minimum. Further, the configuration of the temporary lens which gives the optimum optical characteristic is determined by taking into account the optical characteristics obtained at the respective end points of a plurality of divisions of the offset amount, so that the specifications of the intended ophthalmic lens are advantageously determined.

Referring next to a flow chart of FIG. 4, there will be explained another method of designing an ophthalmic lens according to a fourth embodiment of the invention. The flow chart of FIG. 4 starts with step S41 in which the specifications of a temporary lens which gives the intended ophthalmic lens are determined such that the temporary lens gives an optical power required by a wearer of the ophthalmic lens. The optical power required by the lens wearer is determined by various examinations of the eye to which the intended ophthalmic lens is applied, using various known devices. Based on the knowledge of those skilled in the art of the ophthalmic lens, the configuration of the temporary lens is temporaryly determined, and the specifications of the temporary lens such as a base curve (BC) of a back surface, a front curve (FC) of a front surface, a diameter (DIA), a center thickness (CT), an aspheric coefficient, etc. are determined by taking into account a refractive index of a lens material.

Step S41 is followed by step S42 in which the temporary lens is applied to a suitable schematic eye. The temporary lens applied to the schematic eye is mathematically expressed for calculating the optical characteristic described below.

The schematic eye used in this fourth embodiment is the same as that (the Gullstrand schematic eye in the non-accommodating state) described above with respect to the first embodiment, and a detail explanation of which is dispensed with. As described in the first embodiment, the schematic eye which is approximated to the eye of the wearer of the ophthalmic lens by suitably changing the values of any one of the parameters in the Gullstrancd schematic eye may be used.

Step S42 is followed by step S43 in which the position of the optical axis of the temporary lens is offset by a predetermined offset amount from the optical axis of the schematic eye, such that the temporary lens is located at a stable position on the schematic eye corresponding to a stable position on the eye of the lens wearer in which the ophthalmic lens is held in place. The stable position of the ophthalmic lens on the wearer's eye is determined by actually applying a test lens (ophthalmic lens) to the wearer's eye and obtaining an offset amount of the optical axis of the ophthalmic lens from the optical axis of the wearer's eye while the ophthalmic lens is stably held in place. The temporary lens is located on the stable position on the schematic eye such that the optical axis of the temporary lens is offset from the optical axis of the schematic eye by the offset amount obtained as described above. In designing a standard ophthalmic lens, an average value of the offset amounts corresponding to the different stable positions of the ophthalmic lens on the ordinary lens wearers' eyes is employed. When the ophthalmic lens is a contact lens, the offset amount represented by an angle defined by the intersecting optical axes of the temporary lens and the schematic eye is determined to be not greater than 30°. When the ophthalmic lens is an intraocular lens, the offset amount represented by a distance between the optical axes of the temporary lens and the schematic eye as measured on the cornea of the schematic eye is determined to be not greater than 4 mm.

With the temporary lens being located at the stable position on the schematic eye as described above, the optical characteristic of the optical system consisting of the schematic eye and the temporary lens is obtained. In the following steps S44 through S46, the optical characteristics are successively obtained corresponding to different configurations of the temporary lens, and one of the different configurations of the temporary lens which gives optimum one of the successively obtained optical characteristics is selected.

Described more specifically, while the temporary lens is located at the stable position on the schematic eye with the optical axis of the temporary lens being offset from the optical axis of the schematic eye by the predetermined offset amount (step S43), the optical characteristic of the optical system is obtained (step S44). A plurality of optical characteristics corresponding to the different configurations of the temporary lens are successively obtained (step S45), and one of the configurations of the temporary lens which gives optimum one of the plurality of optical characteristics is selected (step S46).

In step S45, the optical characteristics of the optical system are obtained corresponding to the different configurations of the temporary lens in which at least one parameter of the specifications is changed. In view of the fact that the base curve (BC) of the back surface of the contact lens is generally determined so as to match the radius of curvature of the lens wearer's eye, it is preferable to keep the base curve at a constant value. Accordingly, other parameters such as the front curve (FC) of the front surface, the center thickness (CT), and the aspheric coefficient of the temporary lens are changed to give the different configurations of the temporary lens.

The optical characteristics obtained in steps S44 and S45 are calculated by at least one of the wavefront aberration, PSF, MTF, and resolving power as described in the first embodiment, and a detailed explanation of which is dispensed with. The calculation of the optical characteristic is known in the art, and is effected by using commercially available software packages as described above with respect to the first embodiment.

The optical characteristics are successively obtained corresponding to the different configurations of the temporary lens with the optical axis of the temporary lens being offset from the optical axis of the schematic eye by the predetermined offset amount. From among the successively obtained optical characteristics, the optimum optical characteristic is selected, and one of the different configurations of the temporary lens which gives the optimum optical characteristic is determined.

Step S45 is followed by Step S46 to determine the specifications (such as BC, FC, DIA, CT, and aspheric coefficient) of an intended ophthalmic lens, based on the selected optimum configuration of the temporary lens.

In the method of designing the ophthalmic lens wherein the specifications of the intended ophthalmic lens are determined according to the flow chart of FIG. 4 of the fourth embodiment, the offset amount of the optical axis of the ophthalmic lens from the center of the pupil (the optical axis of the schematic eye) is determined by taking into account the stable position of the ophthalmic lens on the eye model (the schematic eye), in which the lens is stably held in place. The optical characteristics corresponding to the different configurations of the temporary lens are obtained with the optical axis of the temporary lens being offset from the optical axis of the schematic eye by the offset amount determined as described above. In the present method, the optimum one of the different configurations of the temporary lens which gives the optimum one of the plurality of optical characteristics is selected, and the specifications of the intended ophthalmic lens are determined on the basis of the selected optimum configuration of the temporary lens. Accordingly, the ophthalmic lens whose specifications are determined as described above exhibits an excellent optical characteristic irrespective of the movement of the ophthalmic lens on the lens wearer's eye to which the lens is applied. Therefore, ophthalmic lens designed as described above effectively assures improved visual acuity and stability.

The method of designing the ophthalmic lens according to the flow chart of FIG. 4 of the fourth embodiment may be modified so as to include a step of effecting the emmetropization of the optical system. The modified method is indicated by a flow chart of FIG. 5.

The flow chart of FIG. 5 according to a fifth embodiment of the invention is identical with the flow chart of FIG. 4 according to the fourth embodiment, except for step S54. Steps S51 through S53 and steps S55 through S58 in the flow chart of FIG. 5 correspond to Steps S41 through S47 in the flow chart of FIG. 4.

In steps S51 through S53 of the flow chart of FIG. 5 corresponding to steps S41 through S43 of the flow chart of FIG. 4, the temporary lens is applied to the prescribed schematic eye such that the temporary lens is located at a stable position on the schematic eye corresponding to a stable position on the eye of the lens wearer in which the ophthalmic lens is held in place, with the optical axis of the temporary lens being offset from the optical axis of the schematic eye by a predetermined offset amount.

In the following step S54, the emmetropization of the optical system consisting of the schematic eye and the temporary lens which is applied thereto is effected. Described in detail, the emmetropizaion of the optical system is effected with the temporary lens being located at the stable position on the schematic eye, by changing an axial length of the schematic eye, for thereby permitting an image to be formed on the retina of the schematic eye.

Thereafter, steps S55 through S58 are executed in a manner similar to that in steps S44 through S47 of the flow chart of FIG. 4 in the fourth embodiment, for thereby determining the specifications of the intended ophthalmic lens.

In the designing method of the flow chart of FIG. 5 according to the fifth embodiment of the invention wherein the step of effecting the emmetropization of the optical system (step S54) is included, the optimum optical characteristic can be easily selected from among a plurality of optical characteristics corresponding to the different configurations of the temporary lens, as compared with the designing method of the flow chart of FIG. 4 of the fourth embodiment wherein the optimum optical characteristic is selected from among a plurality of optical characteristics which are obtained while the emmetropization of the optical system is effected for the different configurations of the temporary lens by changing the values of the optical power of the lens. Accordingly, the present method permits an easy and accurate designing of the ophthalmic lens.

In producing an intended ophthalmic lens, e.g., a contact lens, based on the specifications determined according to the flow chart of FIGS. 1, 2, 3, 4 or 5 described above, a working operation such as cutting or grinding is effected by using a suitable lens material having a predetermined refractive index, such that the lens material is formed into the intended contact lens having the determined specifications. Alternatively, the intended contact lens is produced by a molding operation in which a monomer is polymerized in a mold cavity of a mold assembly, which mold cavity is formed such that the contact lens to be obtained therein has the base curve (BC), front curve (FC), diameter (DIA), central thickness (CT), and aspheric coefficient according to the determined specifications.

While the presently preferred embodiments of this invention have been described in detail by reference to the flow charts which are representative examples of the invention, it is to be understood that the invention may be otherwise embodied.

Although the principle of the present invention is advantageously employed in designing a contact lens, it is also employed in designing other ophthalmic lenses such as an intraocular lens. Further, the present invention permits designing of the contact lens irrespective of whether a tear lens is present or not during wear of the contact lens.

The ophthalmic lens can be designed according to the present invention irrespective of the sign (+)(−) of the refractive power of the ophthalmic lens. The principle of the present invention can be advantageously employed in designing ophthalmic lenses having various refractive powers, such as a monofocal lens and a multifocal lens.

In the illustrated embodiments, the schematic eye as well as the specifications of the temporary lens is represented by numerical values, for thereby simulating the optical system consisting of the temporary lens and the schematic eye in which the image is formed on the retina of the schematic eye, so as to determine the specifications of the intended ophthalmic lens. The specifications of the ophthalmic lens can be determined by various other techniques which may occur to those skilled in the art.

In the illustrated first and second embodiments, the emmetropization of the optical system consisting of the schematic eye and the temporary lens is effected with the optical axes of the schematic eye and the temporary lens being aligned with each other. The emmetropization may be effected without the optical axes of the schematic eye and the temporary lens being aligned with each other. Although the emmetropization of the optical system is established by changing the axial length of the schematic eye in the illustrated first, second, third, and fifth embodiments, the emmetroizaiton may be established by changing at least one of the axial length of the schematic eye, the radius of curvature of the front surface of cornea, the radius of curvature of the back surface of the cornea, the radius of curvature of the front surface of the crystalline lens, the radius of curvature of the back surface of the crystalline lens, the diameter of the pupil, the optical power of a corrective lens.

It is to be understood that the present invention may be embodied with various other changes, modifications and improvement, which may occur to those skilled in the art, without departing from the spirit and scope of the invention defined in the following claims:

What is claimed is:

1. A method of designing an ophthalmic lens, comprising the steps of:

determining specifications of a temporary lens such that said temporary lens gives an optical power required by a wearer of the ophthalmic lens;

applying said temporary lens to a prescribed schematic eye, and effecting emmetropization of an optical system consisting of said temporary lens and said schematic eye;

obtaining an optical characteristic of said optical system at a position of an optical axis of said temporary lens which is offset from an optical axis of said schematic eye by a predetermined offset amount;

obtaining successively optical characteristics corresponding to different configurations of said temporary lens with said axes of said temporary lens and said schematic eye being offset from each other by said predetermined offset amount;

selecting optimum one of said different configurations of said temporary lens which gives optimum one of the successively obtained optical characteristics; and determining specifications of an intended ophthalmic lens as a final product, based on the selected optimum configuration of said temporary lens.

2. A method according to claim 1, wherein said emmetropization of said optical system is effected with said optical axes of said temporary lens and said schematic eye being aligned with each other.

3. A method according to claim 1, wherein said emmetropization of said optical system is effected by changing at least one of the following parameters selected from the group consisting of: an axial length of said schematic eye, a radius of curvature of a front surface of a cornea of said schematic eye, a radius curvature of a back surface of the cornea of said schematic eye, a radius of curvature of a front surface of a crystalline lens of said schematic eye, a radius of curvature of a back surface of the crystalline lens of said schematic eye, a diameter of a pupil of said schematic eye, and an optical power of a corrective lens.

4. A method according to claim 1, wherein said optical characteristic of said optical system is calculated by at least one of a wavefront aberration, a point spread function (PSF), a modulation transfer function (MTF), and a resolving power.

5. A method according to claim 1, wherein said schematic eye corresponds to an eye of said wearer who wears the ophthalmic lens.

6. A method according to claim 1, wherein the ophthalmic lens is a contact lens, and said predetermined offset amount of said optical axis of said temporary lens from said optical axis of said schematic eye is not greater than 30°.

7. A method according to claim 1, wherein said predetermined offset amount is divided into a plurality of divisions, each division being not greater than 10°, and said optical characteristic is obtained at an end point of each of said plurality of divisions.

8. A method according to claim 1, wherein the ophthalmic lens is an intraocular lens, and said predetermined offset amount of said optical axis of said temporary lens from said optical axis of said schematic eye is not greater than 4 mm.

9. A method according to claim 1, wherein said predetermined offset amount is divided into a plurality of divisions, each division being not greater than 2 mm, and said optical characteristic is obtained at an end point of each of said plurality of divisions.

10. A method of producing an ophthalmic lens based on the specifications determined according the method defined in claim 1.

11. An ophthalmic lens produced according to the method defined in claim 1.

12. A method of designing an ophthalmic lens, comprising the steps of:
   determining specifications of a temporary lens such that said temporary lens gives an optical power required by a wearer of the ophthalmic lens;
   applying said temporary lens to a prescribed schematic eye, and effecting emmetropization of an optical system consisting of said temporary lens and said schematic eye;
   obtaining, as a reference characteristic, an optical characteristic of said optical system at a position of an optical axis of said temporary lens which is aligned with an optical axis of said schematic eye;
   obtaining, as a variable characteristic, an optical characteristic of said optical system at a position of said optical axis of said temporary lens which is offset by a predetermined offset amount from said optical axis of said schematic eye;
   obtaining successively said reference characteristics and said variable characteristics corresponding to different configurations of said temporary lens;
   selecting one of said different configurations of said temporary lens, which gives a minimum difference between said reference characteristic and said variable characteristic; and
   determining specifications of an intended ophthalmic lens as a final product, based on the selected configuration of said temporary lens.

13. A method according to claim 12, wherein said emmetropization of said optical system is effected with said optical axes of said temporary lens and said schematic eye being aligned with each other.

14. A method according to claim 12, wherein said emmetropization of said optical system is effected by changing at least one of the following parameters selected from the group consisting of: an axial length of said schematic eye, a radius of curvature of a front surface of a cornea of said schematic eye, a radius curvature of a back surface of the cornea of said schematic eye, a radius of curvature of a front surface of a crystalline lens of said schematic eye, a radius of curvature of a back surface of the crystalline lens of said schematic eye, a diameter of a pupil of said schematic eye, and an optical power of a corrective lens.

15. A method according to claim 12, wherein an optical characteristic of said optical system is calculated by at least one of a wavefront aberration, a point spread function (PSF), a modulation transfer function (MTF), and a resolving power.

16. A method according to claim 12, wherein said schematic eye corresponds to an eye of said wearer who wears the ophthalmic lens.

17. A method according to claim 12, wherein the ophthalmic lens is a contact lens, and said predetermined offset amount of said optical axis of said temporary lens from said optical axis of said schematic eye is not greater than 30°.

18. A method according to claim 12, wherein said predetermined offset amount is divided into a plurality of divisions, each division being not greater than 10°, and said optical characteristic of said variable characteristic is obtained at an end point of each of said plurality of divisions.

19. A method according to claim 12, wherein the ophthalmic lens is an intraocular lens, and said predetermined offset amount of said optical axis of said temporary lens from said optical axis of said schematic eye is not greater than 4 mm.

20. A method according to claim 12, wherein said predetermined offset amount is divided into a plurality of divisions, each division being not greater than 2 mm, and said optical characteristic of said variable characteristic is obtained at an end point of each of said plurality of divisions.

21. A method of producing an ophthalmic lens based on the specifications determined according the method defined in claim 12.

22. An ophthalmic lens produced according to the method defined in claim 12.

* * * * *